United States Patent [19]

Yu et al.

[11] Patent Number: 5,444,078
[45] Date of Patent: Aug. 22, 1995

[54] FULLY WATER-DILUTABLE MICROEMULSIONS

[75] Inventors: Bing Yu, Horsham; John R. Mattox, Perkasie, both of Pa.

[73] Assignee: Rohm and Haas Company, Philadelphia, Pa.

[21] Appl. No.: 130,614

[22] Filed: Oct. 1, 1993

[51] Int. Cl.[6] ............... A01N 25/02; A01N 25/30; A01N 43/80; C02F 1/50
[52] U.S. Cl. ................... 514/372; 514/772; 514/937; 514/938; 514/941; 514/942; 514/943; 504/138; 504/156; 71/DIG. 1; 422/28; 422/37; 210/749; 210/753; 210/764
[58] Field of Search ........... 514/372, 941, 942, 943, 514/772, 937, 938; 504/156, 138; 71/DIG. 1; 422/28, 37; 210/749, 753, 764

[56] References Cited

U.S. PATENT DOCUMENTS

| 3,683,078 | 8/1972 | Haus | 514/71 |
|---|---|---|---|
| 3,761,488 | 9/1973 | Lewis et al. | 548/213 |
| 4,567,161 | 1/1986 | Posanski et al. | 514/23 |
| 4,895,877 | 1/1990 | Rei et al. | 514/970 |
| 4,904,695 | 2/1990 | Bell | 514/521 |
| 4,954,338 | 9/1990 | Mattox | 514/78 |
| 4,973,352 | 11/1990 | Heinrich et al. | 71/91 |
| 4,995,900 | 2/1991 | Fatcher | 71/92 |
| 5,013,748 | 5/1991 | Radtke et al. | 514/383 |
| 5,200,188 | 4/1993 | Mattox | 424/405 |

FOREIGN PATENT DOCUMENTS 1209361 8/1986 Canada.

OTHER PUBLICATIONS

McCutcheon's Emulsifiers & Detergents, vol. 1, North American Edition, 1990, The Manufacturing Confectioner Publishing Co., N.J., pp. 39, 168, 169, 174, 188 and 190.

*Primary Examiner*—Allen J. Robinson
*Assistant Examiner*—John D. Pak
*Attorney, Agent, or Firm*—Michael B. Fein

[57] ABSTRACT

Microemulsions of water-insoluble active ingredients, employing a special surfactant system and solvent system. These microemulsions remain thermodynamically stable over a wide range of water dilutions.

12 Claims, No Drawings

FULLY WATER-DILUTABLE MICROEMULSIONS

BACKGROUND OF THE INVENTION

1. Field of the Invention

This invention relates to microemulsions of water-insoluble active ingredients suitable for use as fungicides, slimicides, algicides, and bactericides.

2. Description of the Prior Art

Microemulsions containing water-insoluble biocidal or pesticidal agents have been proposed in, for example:

U.S. Pat. No. 5,013,748, which discloses aqueous biocidal microemulsions useful for the protection of wood. The biocidal components employed contain at least one triazole fungicide, at least one quaternary ammonium fungicide and at least one benzimidazole fungicide in a liquid carrier comprising at least two necessary polar solvents. This patent does not teach fully water dilutable systems.

U.S. Pat. No. 4,954,338, which teaches oil-in-water microemulsions of isothiazolones with low water solubility with EO/PO copolymer/artionic sulfates or sulfonates as microemulsifier. The solvents are alkyl alcohols or alkylalkoxylated alcohols. This patent requires the use of EO/PO (ethylene oxide/propylene oxide) copolymer to maintain the microemulsion with dilution by water.

U.S. Pat. No. 4,567,161, which discloses transparent microemulsions with active ingredients (e.g. pesticides, herbicides, pharmaceuticals) together with a phospholipid and a coemulsifier (glycerin ester).

Canadian Patent No. 1209361, which discloses cold stable aqueous microemulsions of agrochemical pesticides, household pest control agents, and pharmaceuticals using an emulsifier which is a mixture of alkylaryl polyglycol and an alkylarylsulfonate salt.

U.S. Pat. No. 4,973,352, which discloses aqueous microemulsions for only herbicidal use containing a combination of a herbicide, one or more emulsifiers or wetting agents such as calcium dodecylbenzenesulfonate, one or more organic solvents and water. This patent also does not teach fully water dilutable microemulsions.

U.S. Pat. No. 4,904,695, which discloses an aqueous based insecticidal microemulsion comprising a swathetic pyrethroid/organophosphate, surfactant blend, adjuvants, such as antifoamers, thickeners and preservatives, and water. The microemulsions of this patent are not fully water dilutable.

U.S. Pat. No. 4,995,900 discloses only w/o microemulsion formulations of water-insoluble herbicides and are, therefore, not fully water dilutable.

Fully water dilutable microemulsions, especially of certain insoluble biocidal active ingredients, have not been previously known and available.

SUMMARY OF THE INVENTION

It is an object of the invention to provide fully water dilutable microemulsions of low water soluble (less than 1% by weight in) active ingredients. By fully water dilutable is meant a microemulsion which is water-dilutable from water-free concentrates (referred to as microemulsion concentrates) to microemulsion containing large concentrations of water.

This object, and others which will become apparent from the following disclosure, is achieved by the present invention which comprises in one aspect a composition comprising:

(A) one or more active ingredient compounds which are less than 1000 ppm soluble in water at room temperature and having a melting point of less than 100° C.;

(B) one or more non-polar, water immiscible solvent selected front the group consisting of benzyl alcohol, benzyl acetate, pine oil, phenethyl alcohol, xylene, phenoxyethanol, butyl phthalate, 2,2,4-trimethyl-1,3-pentanediol monoisobutyrate, and alkylbenzene, said solvent being capable of dissolving at least 5% by weight of (A) at room temperature;

(C) a surfactant system comprised of:
  (C1) one or more sulfated of sulfonated anionic surfactants having about 3-17% sulfation or sulfonation, selected from the group consisting of sulfated and/or sulfonated castor oil, sulfated and/or sulfonated ethoxylated alkylphenols, sulfated and/or sulfonated ethoxylated fatty alcohols, sulfated and/or sulfonated fatty acids, and sulfated alkanolamides; and
  (C2) one or more ethoxylated surfactant selected from the group consisting of ethoxylated ($C_{10}$–$C_{18}$)alkyl phosphate monoesters and/or diesters and/or triesters, ethoxylated ($C_{10}$–$C_{18}$) alkaryl phosphated monoesters and/or diesters, ethoxylated ($C_8$–$C_{20}$)monoalkyl- or dialkylphenols, ethoxylated alkylamides, ethoxylated alkanols, and ethoxylated castor oil; and (D) 0 to 99.9 % by weight water;
  the weight ratio of (C1) to (C2) being about 10/90 to 90/10;
  the weight ratio of said (A) to (B) being about 95/5 to about 1/99, and
  the weight ratio of said (A) to (C) being about 1/99 to about 86/14;
  said composition being thermodynamically stabile and clear, opalescent, or only slightly cloudy at all levels of water dilution up to 99%.

In another aspect, the invention comprises a method for inhibiting the growth bacteria, fungi, and algae.

DETAILED DESCRIPTION AND THE PREFERRED EMBODIMENTS

The microemulsions of the invention are useful in many areas of preservation and agricultural applications, depending on the activity of the active ingredient. The isothiazolones, for example, are active as disinfectants, sanitizers, cleaners, deodorizers, liquid and powder soaps, skin removers, oil and grease removers, food processing chemicals, wood preservation, polymer latices, pair, lazures, stains, mildewcides, hospital and medical antiseptics, medical devices, metal working fluids, cooling water, air washers, petroleum protection, paper treatment, pulp and paper slurries, paper mill slimicides, petroleum products, adhesives, textiles, pigment slurries, latexes, leather and hide treatment, petroleum fuel, jet fuel, laundry sanitizers, agricultural formulations, inks, mining, nonwoven fabrics, petroleum storage, rubber, sugar processing, tobacco, swimming pools, photographic rinses, cosmetics, toiletries, pharmaceuticals, chemical toilets, household laundry products, diesel fuel additives, waxes and polishes, oil field applications, and many other applications where water and organic materials come in contact under conditions which allow the growth of undesired microorganisms. Other active ingredients are useful as fungicides, miticides, herbicides, insecticides, and plants growth regulators.

Preferred active ingredients are microbicides. Especially preferred are 4,5-dichloro-2-n-octyl-3-isothiazolone, and 2-n-octyl-3-isothiazolone. Other preferred active ingredients are agricultural fungicides, for example 2-chloro-1-(3-ethoxy-4-nitrophenoxy)-4-(trifluoromethyl) benzene, 2,4-dinitro-6-octyl-phenyl-crotonate, and alph-butyl-alph-(4-chlorophenyl)-1H-1,2,4-triazole-1-propanenitrile.

In general, one or more active ingredient compounds which are less than 1000 ppm soluble in water at room temperature and having a melting point of less than 100° C. can be used in the invention.

One or more non-polar, water immiscible solvent selected from the group consisting of benzyl alcohol, benzyl acetate, pine oil, phenethyl alcohol, xylene, phenoxyethanol, butyl phthalate, 2,2,4-trimethyl-1,3-pentanediol monoisobutyrate, and alkylbenzene, said solvent being capable of dissolving at least 5% by weight of (A) at room temperature, is used to dissolve the active ingredient(s).

A surfactant system comprising two different surfactants is used. The first surfactant comprises one or more sulfated of sulfonated anionic surfactants having about 3-17% sulfation or sulfonation, selected from the group consisting of sulfated and/or sulfonated castor oil, sulfated and/or sulfonated ethoxylated alkylphenols, sulfated and/or sulfonated ethoxylated fatty alcohols, sulfated and/or sulfonated fatty acids, and sulfated alkanolamides. The second surfactant comprises one or more ethoxylated surfactant selected from the group consisting of ethoxylated ($C_{10}$–$C_{18}$)alkyl phosphate monoesters and/or diesters and/or triesters, ethoxylated ($C_{10}$–$C_{18}$)alkaryl phosphated monoesters and/or diesters, ethoxylated ($C_8$–$C_{20}$)monoalkyl- or dialkyl-phenols, ethoxylated alkylamides, ethoxylated alkanols, and ethoxylated castor oil.

Microemulsion concentrates without water can be prepared according to the invention, as can microemulsions comprising up to 99.9% by weight water. As mentioned above, the compositions of the invention remain microemulsions at all levels of water dilution, one of the important novel features of the invention. The composition remains thermodynamically stabile and clear, opalescent, or only slightly cloudy at all levels of water dilution up to 99.9%.

Weight ratio of the first surfactant to the second surfactant are about 10/90 to 90/10. Weight ratios of the active ingredient(s) to solvent(s) are about 95/5 to about 1/99 weight ratios of active ingredient(s) to surfactant system are about 1/99 to about 86/14.

Various adjuvants including antifoam agents, such as the commercially available silicone antifoam emulsions, and the like can be included, for example antifreeze agents such as propylene glycol, urea, and the like; water soluble inorganic salts, such as sodium chloride, magnesium sulfate, and the like which are used to optimize the action of the surfactant because it increases the concentration of the surfactant at the interface of the microemulsion; wetting agents; thickeners; defoamers; and the like.

The microemulsion concentrates of the invention can be prepared by dissolving solid active ingredient in an organic solvent to form the oil phase. The surfactants can then be added to the oil phase, either individually or in combination. The resulting mixture is gently stirred or agitated to give a microemulsion concentrate. Alternatively, if the solid active ingredient is heat stable, all the components may be added together in a single vessel and the vessel heated slightly to form the microemulsion concentrate. This has the advantage that it is a one step addition. When the active ingredient is a liquid, either approach will work. A liquid active ingredient may be used itself as the oil phase without the addition of an organic solvent. It is preferred that an organic solvent be used to dissolve the active ingredient to form the oil phase. It is further preferred that the oil phase be formed first and the surfactants added to it.

The microemulsions of the invention may be prepared by diluting a microemulsion concentrate with water. Alternatively, a microemulsion may be prepared directly without going through a concentrate form. This is accomplished by simply adding the desired amount of water along with the surfactants in the same manner as described for the micoemulsion concentrates. Both methods of microemulsion formation are preferred.

Certain microemulsions of the invention can be diluted with either soft (e.g. deionized) or hard water.

The following examples set forth a few embodiments of the invention. All parts and percentages are by weight unless otherwise indicated.

EXAMPLES

Example 1—Formulations

Table 1 shows the composition of microemulsion concentrates and microemulsions used in the following examples. These samples were prepared by dissolving the active ingredient ("AI") in an organic solvent to yield an oil phase. To this oil phase were combined the desired surfactants to yield the microemulsion concentrate ("MC") samples. The microemulsions ("ME's") were prepared by diluting the MC's with water.

The abbreviations used in the following Tables and example are as follows:

| Active Ingredient | |
|---|---|
| AI 1 = 4,5-dichloro-2-n-octyl-3-isothiazolone | |
| AI 2 = 2-n-octyl-3-isothiazolone | |
| Solvent # | Name |
| 1 | Benzyl alcohol |
| 2 | Benzyl acetate |
| 3 | Pine oil/benzyl alcohol (1/1) |
| 4 | Pine oil |
| 5 | Xylene/benzyl alcohol (1:1) |
| 6 | Aromatic 100 ® (a mixture of alkylbenzenes) |
| 7 | Aromatic 150 ® (a mixture of alkylbenzenes) |
| 8 | Pine oil/benzyl acetate (1/1) |
| 9 | Xylene/pine oil (1/1) |
| 10 | Phenethyl alcohol |
| 11 | Butyl phthalate |
| 12 | 2-Phenoxyethanol |
| 13 | Xylene |
| 14 | 2,2,4-trimethyl-1,3-pentanediol monoisobutyrate |
| Surfactant | Sulfated or Sulfonated Anionic Surfactants (Class C1) |
| A | 70% Sulfated castor oil in aqueous (aq) solution |
| B | 79% Sulfonated castor oil in aq solution |
| C | 100% Sodium ($C_{12}$—$C_{16}$)alkylphenol polyether sulfate |
| D | 70% Sulfated fatty acid (6–8% $SO_3$) in aq solution |
| | Ethoxylated Surfactants (Class C2) |
| E | 100% Free aliphatic acid of a complex organic phosphate ester |
| F | 100% Ethoxylated (EO 9–10) octylphenol |
| G | 100% Ethoxylated (EO 15) dinonylphenol |
| H | 100% Ethoxylated (EO 13) dodecylphenol |

| | |
|---|---|
| I | 100% Ethoxylated (EO 9-10) nonylphenol |
| J | 100% Ethoxylated (EO 5) cocamide |
| K | 100% Ethoxylated (EO 30) castor oil |
| L | 100% ($C_9$—$C_{11}$) Linear primary ethoxylate (EO/alcohol molar ratio of 8) |

TABLE 1

Microemulsion Concentrates ("MC") and Microemulsions ("ME")

| Sample | MC or ME | % AI 1 | % AI 2 | Solvent (%) | % Water | Surfactant C1 (%) | Surfactant C2 (%) |
|---|---|---|---|---|---|---|---|
| 1 | MC | 9.0 | 0 | 1 (21.0) | 0 | A (49.0) | E (21.0) |
| 2 | MC | 16.0 | 0 | 1 (24.0) | 0 | A (42.0) | E (18.0) |
| 3 | MC | 9.0 | 0 | 3 (21.0) | 0 | A (49.0) | E (21.0) |
| 4 | MC | 9.0 | 0 | 2 (21.0) | 0 | A (49.0) | E (21.0) |
| 5 | MC | 9.0 | 0 | 10 (21.0) | 0 | A (49.0) | E (21.0) |
| 6 | MC | 9.0 | 0 | 4 (21.0) | 0 | A (49.0) | E (21.0) |
| 7 | ME | 3.6 | 0 | 5 (8.4) | 60 | A (19.6) | E (8.4) |
| 8 | ME | 4.5 | 0 | 6 (10.5) | 50 | A (24.5) | E (10.5) |
| 9 | ME | 4.5 | 0 | 7 (10.5) | 50 | A (24.5) | E (10.5) |
| 10 | MC | 9.0 | 0 | 8 (21.0) | 0 | A (49.0) | E (21.0) |
| 11 | ME | 3.6 | 0 | 9 (8.4) | 60 | A (19.6) | E (8.4) |
| 12 | ME | 4.5 | 0 | 11 (10.5) | 50 | A (24.5) | E (10.5) |
| 13 | MC | 0 | 9.0 | 1 (21.0) | 0 | A (49.0) | E (21.0) |
| 14 | MC | 0 | 12.0 | 1 (28.0) | 0 | A (42.0) | E (18.0) |
| 15 | MC | 6.0 | 6.0 | 1 (28.0) | 0 | A (42.0) | E (28.0) |
| 16 | MC | 10.0 | 10.0 | 1 (21.0) | 0 | A (42.0) | E (28.0) |
| 17 | MC | 9.0 | 3.0 | 1 (21.0) | 0 | A (46.9) | E (20.1) |
| 18 | MC | 6.0 | 12.0 | 1 (22.0) | 0 | A (42.0) | E (18.0) |
| 19 | MC | 9.0 | 0 | 1 (21.0) | 0 | B (49.0) | E (21.0) |
| 20 | MC | 0 | 9.0 | 1 (21.0) | 0 | B (49.0) | E (21.0) |
| 21 | MC | 6.0 | 6.0 | 1 (28.0) | 0 | B (42.0) | E (18.0) |
| 22 | MC | 9.0 | 0 | 1 (21.0) | 0 | A (28.0) | F (42.0) |
| 23 | MC | 9.0 | 0 | 2 (21.0) | 0 | A (28.0) | F (42.0) |
| 24 | ME | 4.5 | 0 | 10 (10.5) | 50 | A (14.0) | F (21.0) |
| 25 | ME | 4.5 | 0 | 9 (10.5) | 50 | A (14.0) | F (21.0) |
| 26 | MC | 9.0 | 0 | 5 (21.0) | 0 | A (35.0) | F (35.0) |
| 27 | MC | 9.0 | 0 | 4 (21.0) | 0 | A (31.5) | F (38.5) |
| 28 | MC | 9.0 | 0 | 8 (21.0) | 0 | A (28.0) | F (42.0) |
| 29 | MC | 9.0 | 0 | 3 (21.0) | 0 | A (30.0) | F (40.0) |
| 30 | ME | 5.4 | 0 | 13 (12.6) | 40 | A (16.8) | F (25.2) |
| 31 | MC | 9.0 | 0 | 11 (21.0) | 0 | A (28.0) | F (42.0) |
| 32 | MC | 0 | 12.0 | 1 (18.0) | 0 | A (28.0) | F (42.0) |
| 33 | MC | 6.0 | 8.0 | 1 (26.0) | 0 | A (24.0) | F (36.0) |
| 34 | MC | 15.0 | 0 | 1 (15.0) | 0 | B (28.0) | F (42.0) |
| 35 | MC | 9.0 | 0 | 2 (21.0) | 0 | B (35.0) | F (35.0) |
| 36 | MC | 0 | 16.0 | 1 (24.0) | 0 | B (24.0) | F (36.0) |
| 37 | MC | 9.0 | 0 | 1 (21.0) | 0 | A (49.0) | G (21.0) |
| 38 | MC | 9.0 | 0 | 2 (21.0) | 0 | A (44.0) | G (26.0) |
| 39 | MC | 9.0 | 0 | 3 (21.0) | 0 | A (49.0) | G (21.0) |
| 40 | MC | 9.0 | 0 | 3 (21.0) | 0 | A (42.0) | G (28.0) |
| 41 | MC | 6.0 | 0 | 5 (24.0) | 0 | A (49.0) | G (21.0) |
| 42 | MC | 9.0 | 0 | 8 (21.0) | 0 | A (42.0) | G (28.0) |
| 43 | MC | 6.0 | 0 | 5 (24.0) | 0 | A (38.5) | G (31.5) |
| 44 | MC | 9.0 | 0 | 5 (21.0) | 0 | A (38.5) | G (31.5) |
| 45 | MC | 9.0 | 0 | 1 (21.0) | 0 | A (28.0) | H (42.0) |
| 46 | MC | 9.0 | 0 | 1 (21.0) | 0 | A (25.0) | I (45.0) |
| 47 | MC | 15.0 | 0 | 1 (15.0) | 0 | C (28.0) | G (42.0) |
| 48 | MC | 9.0 | 0 | 1 (21.0) | 0 | A (33.0) | J (37.0) |
| 49 | MC | 9.0 | 0 | 1 (21.0) | 0 | A (49.0) | K (21.0) |
| 50 | MC | 15.0 | 0 | 1 (15.0) | 0 | B (35.0) | L (35.0) |
| 51 | MC | 9.0 | 0 | 1 (21.0) | 0 | D (49.0) | E (21.0) |
| 52 | MC | 9.0 | 0 | 14 (21.0) | 0 | D (49.0) | E (21.0) |

Example 2—Water Dilutability

The water dilutability of the MC and ME's of Example 1 was determined by adding varying amounts of deionized water and evaluating clarity using a rating scale of 0–5. Sufficient water was added to the samples to form dilutions containing from 10 to 98% water by weight. The rating scale is defined as follows:

0 = perfectly clear;
1 = clear, very slight opalescence;
2 = opalescent;
3 = opalescent, slightly cloudy;
4 = cloudy (macroemulsion); and
5 = phase separation.

A rating of 3 or lower is considered passing. These results are shown in Table 2.

TABLE 2

Water Dilutability of ME Samples

| % Water by Weight: | 0 | 10 | 20 | 30 | 40 | 50 | 60 | 70 | 80 | 90 | 95 | 98 |
|---|---|---|---|---|---|---|---|---|---|---|---|---|
| Sample # | | | | | | | | | | | | |
| 1 | 3 | 0 | 0 | 0 | 0 | 0 | 0 | 0 | 0 | 0 | 0 | 0 |
| 2 | 3 | 3 | 2 | 1 | 0 | 0 | 0 | 0 | 0 | 0 | 0 | 0 |
| 3 | 2 | 1 | 1 | 0 | 0 | 0 | 0 | 0 | 0 | 0 | 0 | 0 |
| 4 | 0 | 0 | 1 | 2 | 3 | 4 | 3 | 2 | 0 | 0 | 0 | 0 |
| 5 | 2 | 2 | 2 | 1 | 0 | 0 | 0 | 0 | 0 | 0 | 0 | 0 |
| 6 | 0 | 0 | 0 | 1 | 2 | 2 | 1 | 0 | 0 | 0 | 0 | 0 |
| 7 | — | — | — | — | — | 2 | 1 | 0 | 0 | 0 | 0 | 0 |
| 8 | — | — | — | — | — | 1 | 3 | 1 | 0 | 0 | 0 | 0 |
| 9 | — | — | — | — | — | 1 | 3 | 0 | 0 | 0 | 0 | 0 |
| 10 | 0 | 0 | 0 | 1 | 1 | 2 | 2 | 0 | 0 | 0 | 0 | 0 |
| 11 | — | — | — | — | — | 1 | 0 | 0 | 0 | 0 | 0 | 0 |
| 12 | — | — | — | — | — | 3 | 2 | 0 | 0 | 0 | 0 | 0 |
| 13 | 2 | 1 | 0 | 0 | 0 | 0 | 0 | 0 | 0 | 0 | 0 | 0 |
| 14 | 3 | 3 | 2 | 2 | 2 | 0 | 0 | 0 | 0 | 0 | 0 | 0 |
| 15 | 3 | 3 | 3 | 1 | 0 | 0 | 0 | 0 | 0 | 0 | 0 | 0 |
| 16 | 3 | 3 | 2 | 2 | 0 | 0 | 0 | 0 | 0 | 0 | 0 | 0 |
| 17 | 3 | 3 | 2 | 1 | 0 | 0 | 0 | 0 | 0 | 0 | 0 | 0 |
| 18 | 3 | 3 | 1 | 1 | 0 | 0 | 0 | 0 | 0 | 0 | 0 | 0 |
| 19 | 2 | 0 | 0 | 0 | 0 | 0 | 0 | 0 | 0 | 0 | 0 | 0 |
| 20 | 3 | 2 | 0 | 0 | 0 | 0 | 1 | 0 | 0 | 0 | 0 | 0 |
| 21 | 3 | 1 | 0 | 0 | 0 | 0 | 0 | 0 | 0 | 0 | 0 | 0 |
| 22 | 0 | 0 | 0 | 0 | 0 | 0 | 0 | 0 | 0 | 0 | 0 | 0 |
| 23 | 0 | 0 | 0 | 0 | 1 | 2 | 2 | 0 | 0 | 0 | 0 | 0 |
| 24 | — | — | — | — | 1 | 0 | 0 | 0 | 0 | 0 | 0 | 0 |
| 25 | — | — | — | — | 2 | 0 | 0 | 0 | 0 | 0 | 0 | 0 |
| 26 | 0 | 0 | 0 | 1 | 2 | 3 | 0 | 0 | 0 | 0 | 0 | 0 |
| 27 | 0 | 0 | 0 | 0 | 1 | 3 | 0 | 0 | 0 | 0 | 0 | 0 |
| 28 | 0 | 0 | 0 | 0 | 1 | 2 | 1 | 0 | 0 | 0 | 0 | 0 |
| 29 | 0 | 0 | 0 | 0 | 1 | 2 | 0 | 0 | 0 | 0 | 0 | 0 |
| 30 | — | — | — | — | 1 | 2 | 0 | 0 | 0 | 0 | 0 | 0 |
| 31 | 2 | 1 | 1 | 1 | 1 | 0 | 0 | 0 | 0 | 0 | 0 | 0 |
| 32 | 0 | 0 | 0 | 0 | 0 | 0 | 0 | 0 | 0 | 0 | 0 | 0 |
| 33 | 0 | 3 | 2 | 0 | 0 | 0 | 0 | 0 | 0 | 0 | 0 | 0 |
| 34 | 0 | 0 | 0 | 0 | 0 | 0 | 0 | 0 | 0 | 0 | 0 | 0 |
| 35 | 0 | 1 | 0 | 0 | 0 | 0 | 0 | 0 | 0 | 0 | 0 | 0 |
| 36 | 0 | 0 | 1 | 0 | 0 | 0 | 0 | 0 | 0 | 0 | 0 | 0 |
| 37 | 2 | 1 | 0 | 0 | 0 | 0 | 0 | 0 | 0 | 0 | 0 | 0 |
| 38 | 0 | 0 | 0 | 0 | 0 | 2 | 2 | 0 | 0 | 0 | 0 | 0 |
| 39 | 0 | 0 | 0 | 0 | 1 | 2 | 0 | 0 | 0 | 0 | 0 | 0 |
| 40 | 0 | 0 | 0 | 0 | 1 | 2 | 0 | 0 | 0 | 0 | 0 | 0 |
| 41 | 0 | 0 | 0 | 0 | 2 | 3 | 0 | 0 | 0 | 0 | 0 | 0 |
| 42 | 0 | 0 | 0 | 0 | 2 | 2 | 1 | 0 | 0 | 0 | 0 | 0 |
| 43 | 0 | 0 | 0 | 1 | 1 | 0 | 0 | 0 | 0 | 0 | 0 | 0 |
| 44 | 0 | 0 | 0 | 1 | 1 | 0 | 0 | 0 | 0 | 0 | 0 | 0 |
| 45 | 0 | 0 | 0 | 0 | 0 | 0 | 0 | 0 | 0 | 0 | 0 | 0 |
| 46 | 0 | 0 | 0 | 0 | 0 | 0 | 0 | 0 | 0 | 0 | 0 | 0 |
| 47 | 0 | 0 | 1 | 1 | 1 | 2 | 2 | 0 | 0 | 0 | 0 | 0 |
| 48 | 2 | 0 | 0 | 0 | 0 | 0 | 0 | 0 | 0 | 0 | 0 | 0 |
| 49 | 2 | 2 | 0 | 0 | 0 | 0 | 0 | 0 | 0 | 0 | 0 | 0 |
| 50 | 1 | 1 | 0 | 0 | 0 | 0 | 0 | 0 | 0 | 1 | 0 | 0 |
| 51 | 2 | 3 | 3 | 2 | 2 | 0 | 0 | 0 | 0 | 0 | 0 | 0 |
| 52 | 3 | 3 | 0 | 0 | 0 | 0 | 0 | 0 | 0 | 0 | 0 | 0 |

Example 3—Comparative

To demonstrate the importance of the surfactant system, MC's of the invention were compared to MC's having different surfactant systems with regard to water dilutability. The samples were prepared by combining the surfactant(s) listed below with an oil phase. The ratio of oil phase to surfactant was 30/70 for each sample. The oil phase was a mixture of AII and solvent 2 in a ratio of 30/70. Once the surfactant(s) and oil phase were combined (0% water), varying amounts of water were added as described in Example 2. The rating scale of 0–5 described in Example 2 was used to evaluate the clarity of the dilutions. In some instances, the comparative samples gelled. This gelled phase is properly termed a liquid crystal phase and is denoted by LC in the ratings in Table 3. The surfactants are as described in Example 1 or as described below.

| Surfactant System | Surfactant(s) |
| --- | --- |
| 53 (invention) | A and E in a ratio of 70/30 |
| 54 (invention) | A and I in a ratio of 60/40 |
| 55 (invention) | A and I in a ratio of 55/45 |
| 56 (invention) | Sulfated oleic acid (30% aq) and E in a ratio of 70/30 |
| 57 (comparative) | A (single component) |
| 58 (comparative) | B (single component) |
| 59 (comparative) | E (single component) |
| 60 (comparative) | A and ethoxylated sorbitan monooleate in a ratio of 30/70 |
| 61 (comparative) | Sodium dodecylbenzenesulfonate (65% aq) and E in a ratio of 40/60 |
| 62 (comparative) | Calcium dodecylbenzenesulfonate and K in a ratio of 20/80 |

TABLE 3

| | Water Dilutability | | | | | | | | | | | |
| --- | --- | --- | --- | --- | --- | --- | --- | --- | --- | --- | --- | --- |
| % Water by Weight: | 0 | 10 | 20 | 30 | 40 | 50 | 60 | 70 | 80 | 90 | 95 | 98 |
| Invention: | | | | | | | | | | | | |
| 53 | 0 | 0 | 0 | 0 | 0 | 0 | 0 | 0 | 0 | 0 | 0 | 0 |
| 54 | 0 | 0 | 0 | 0 | 0 | 0 | 0 | 0 | 0 | 0 | 0 | 0 |
| 55 | 0 | 0 | 0 | 0 | 0 | 0 | 0 | 0 | 0 | 0 | 0 | 0 |
| 56 | 0 | 3 | 2 | 2 | 0 | 0 | 0 | 0 | 0 | 0 | 0 | 0 |
| Comparative: | | | | | | | | | | | | |
| 57 | 0 | 0 | 5 | LC | LC | 5 | 5 | 5 | 1 | 0 | 0 | 0 |
| 58 | 0 | 5 | 5 | 5 | LC | 5 | 5 | 5 | 2 | 1 | 0 | 0 |
| 59 | 0 | 5 | 5 | 5 | 5 | 5 | 5 | 5 | 3 | 2 | 2 | 1 |
| 60 | 5 | 5 | 5 | 5 | 5 | 5 | 5 | 5 | 5 | 5 | 5 | 5 |
| 61 | 0 | 0 | 0 | 5 | 5 | LC | LC | 5 | 5 | 2 | 1 | 1 |
| 62 | 0 | 5 | 5 | 5 | 5 | 5 | 5 | 5 | 5 | 5 | 5 | 5 |

Example 4—Biological Activity

The ME's of the invention were evaluated for biological activity. The MC of Sample I from Table I was diluted with water, and a defoaming agent, a silicone emulsion containing methylated silica, polyethylene glycol sorbitan tristearate, glycerol monostearate, polyethylene glycol stearate, and methylcellulose (Antifoam 1520-US®) was added to yield an ME. This ME had the following composition:

| | % |
| --- | --- |
| AI 1 | 2.1 |
| Solvent 1 | 7.9 |
| Surfactant A | 16.3 |
| Surfactant E | 7.0 |
| water | 66.3 |
| defoaming agent | 0.4 |

This ME was used in the following studies.

A. Oxygen Uptake Studies

Oxygen uptake is one of the indicators of microbial activity (respiration). Monitoring dissolved oxygen provides a quick and simple method for determining the effect of a biocide on aerobic microorganisms. A series of oxygen uptake studies were performed to determine the effects of the ME on the aerobic respiration of pulp and paper bacteria.

The studies to evalute the ME of the invention were performed using a mixture of bacteria recovered from an actual papermill system (French Paper Mill, Niles, Mich.). The predominant bacterium in the mixture was Pseudomonas. Nutrients (glucose and yeast extract) were added to the papermill stream sample and grown overnight (25° C.). The culture was washed three times (5,000 rpm, 5 min) in 0.1M phosphate buffer and standardized to an optical density (660nm) providing $10^8$ bacteria/ml. One-ml aliquots were added to the test samples for a final concentration of $10^6$ bacteria/ml.

Respiration studies were conducted in 60 ml biochemical oxygen demand (BOD) bottles containing enriched swathetic white water ("SWW") (see below). The SWW was pre-incubated at 25° C. and bubbled with air to achieve oxygen saturation. The concentration of dissolved oxygen (DO) was measured with a YSI brand Dissolved Oxygen Meter (Model 54A) and Probe (Model 5750). An initial dissolved oxygen concentration was determined while stirring continuously. One-ml of the bacterial inoculum was then added to the test samples, followed by addition of the biocide containing ME. The studies were conducted at 25 ° C. and pH 7. Dissolved oxygen was measured at various time points.

The effect of the active ingredient at various use levels of the ME on oxygen uptake by bacteria was determined over a 6.3 hour period. Both the inoculum and biocides were added to the SWW at the start of the test. DO concentrations were measured over time. A control containing only enriched SWW and the inoculum was included in the test. The results are shown in Table 4.

| Enriched Synthetic White Water Composition | |
| --- | --- |
| Component | mg/l |
| $CaCl_2$ | 111 |
| $MgSO_4$ | 60 |
| $NaHCO_3$ | 168 |
| $K_2HPO_4$ | 140 |
| $NH_4Cl$ | 480 |
| Dextrose | 3,000 |
| Yeast Extract | 1,000 |
| $FeCl_3.6H_2O$ | 1.04 |
| $Na_2$-EDTA | 1.48 |
| Hepes Buffer | 0.05 M |
| Deionized Water | 1 liter |

The total hardness of the SWW was 150 ppm (measured as $CaCO_3$) and the total alkalinity was 100 ppm (measured as $CaCO_3$).

TABLE 4

Effect of ME on Oxygen Uptake
Measure of Dissolved Oxygen (ppm)

| Time (hr) | Control | AI Level | | |
|---|---|---|---|---|
| | | 0.5 ppm | 1.5 ppm | 3 ppm |
| 0.0 | 8.2 | 8.00 | 8.47 | 8.21 |
| 0.5 | 8.04 | 7.97 | 8.42 | 7.97 |
| 1.0 | 7.66 | 7.82 | 8.23 | 7.69 |
| 1.7 | 7.20 | 7.69 | 8.03 | 7.73 |
| 2.0 | 6.96 | 7.62 | 7.95 | 7.76 |
| 3.1 | 5.68 | 7.46 | 7.84 | 7.59 |
| 4.1 | 3.12 | 7.37 | 7.79 | 7.51 |
| 4.6 | 1.14 | 7.36 | 7.76 | 7.45 |
| 5.0 | 0.05 | 7.24 | 7.74 | 7.43 |
| 6.3 | 0.01 | 7.13 | 7.61 | 7.27 |

The above data show that the amount of DO decreases with time in the control sample. This oxygen consumption is indicative of aerobic microorganism activity. The treated samples show little loss of DO indicating an inhibition of microbial activity.

B. Pulp and Paper Evaluations

The nutrients, temperature, pH and dynamics of paper machine systems are ideal for the growth of microorganisms. Organisms in the process water (white water) may attach to surfaces to form biofilm and slime. Slime formation leads to operating problems (paper breaks, plugged pipe work, corrosion) and poor paper quality (stains, holes and odors). Treatment with biocides is important for adequate system operation and quality paper products. The performance of ME described above in controlling bacteria and fungi in pulp and paper systems was evaluated.

The bacterial inoculum evaluated in these studies consisted of cultures of *Pseudomonas aeruginosa* (ATCC#15442), *Enterbacter aerogenes* (ATCC#13048), *Klebsiella pneumoniae* (ATCC#13883) and a gram negative, wild paperslime isolate. The bacterial isolates were transferred from a 25% glycerol stock (0.1 ml) into a shake flask containing sterile enriched synthetic white water (see above). After incubation at 37° C. for 24 hours, the pure cultures were washed three times in a 0.1 M phosphate buffer by centrifugation. Each organism was standardized to a predetermined optical density reading at 660 nm to give $10^8$ organisms/ml. The suspensions were checked for purity prior to testing.

The washed cultures could be used for 4 weeks if stored at 4° C. Viability studies showed no adverse effects from storage.

Prior to testing, the pure cultures were warmed to 37° C. and combined.

A 1% pulp slurry was prepared by homogenzing dry kraft pulp in synthetic white water (see below). All of the synthetic white water components were prepared as sterile stock solutions and added to sterile deionized (DI) water separately. The suspension was adjusted to pH 5 or pH 8 with hydrochloric acid or sodium hydroxide, respectively. This was done in order to evaluate the efficacy of the ME under acidic and alkaline conditions. Aliquots (24 g) were sterilized by autoclaving (121° C., 15 min.). Sterile deionzed water (DI) was added to each sample after it cooled to replace water lost during sterilization.

Synthetic White Water for Pulp Slurry

| Component | mg/l | Purpose |
|---|---|---|
| $CaCl_2$ | 111 | Hardness |
| $MgSO_4$ | 60 | Hardness |
| $NaHCO_3$ | 168 | Alkalinity |
| $K_2HPO_4$ | 28 | Nutrient |
| $NH_4Cl$ | 96 | Nutrient |
| Dextrose | 25 | Nutrient |
| $FeCl_3.6H_2O$ | 1.04 | Trace metal |
| $Na_2$-EDTA | 1.48 | Iron chelator |
| Hepes Buffer | 0.05 M | Buffering |
| Deionized Water | 1 liter | |

The pulp slurry was warmed to 37° C. and then inoculated with one-ml of the mixed bacterial or fungal cultures. The samples were treated with the ME formulation described above at concentrations ranging from 1 to 10 ppm active ingredient (AI). A control containing only SWW and the innoculum was included in the test. Test samples were incubated at 37° C. with shaking for 24 hours. Bacterial and fungal enumerations were done on the liquid portion of the slurry at zero time and after 3, 16, and 24 hours. Viable cells were measured in 96-well microliter plates using an eight-well Most Probable Number (MPN) method. The recovery medium was Trypticase Soy Broth and the level of detection of growth was <6 organisms/mi.

Treatment levels which gave $\geq$1-log reduction in viable cell counts over the 3 to 6 hour time period relative to the untreated control were considered effective. These results are reported in Table 5.

TABLE 5

Measure of Cell Viability (log bacteria/ml)

| pH | Time (hr) | Control | Active Ingredient Level | | |
|---|---|---|---|---|---|
| | | | 1 (ppm) | 2 (ppm) | 5 (ppm) |
| 5 | 0 | 6.493 | 6.493 | 6.493 | 6.493 |
| | 3 | 6.493 | 5.672 | 5.758 | 4.910 |
| | 6 | 7.064 | 7.064 | 5.493 | 4.065 |
| | 24 | 7.258 | 6.910 | 6.258 | 4.758 |
| 8 | 0 | 6.624 | 6.624 | 6.624 | 6.624 |
| | 3 | 7.037 | 6.258 | 5.064 | 3.493 |
| | 6 | 7.758 | 7.064 | 6.037 | 5.064 |
| | 24 | 7.064 | 6.064 | 7.190 | 7.910 |

Example 5—ME Physical Stability

The ME's of the invention were evaluated for their heat and cold physical stability and stability to freeze-thaw cycles. ME's 1A -1P were prepared by diluting with water a ME concentrate comprising solvent 1, AI 1, and surfactant A and surfactant E in a 70/30 ratio to form use dilutions. ME's 2A-2P were prepared by diluting with water a ME concentrate comprising solvent 3, AI 1, and surfactant A and surfactant H in a 60/40 ratio to form use dilutions. To these use dilutions was added a defoaming agent, Antifoam 1520-US ®. The resultant compositions of these formulations are reported in Table 6.

TABLE 6

Samples for Thermal Stability Tests

| Sample | Solvent (%) | AI (%) | Surfactants (%) | Defoamer (%) | % Water |
|---|---|---|---|---|---|
| 1A | 6.0 | 1.7 | 23.37 | 0.40 | 68.54 |
| 1B | 6.0 | 2.0 | " | " | 68.23 |
| 1C | 6.0 | 2.3 | " | " | 67.92 |
| 1D | 7.0 | 1.7 | " | " | 67.54 |
| 1E | 7.0 | 2.0 | " | " | 67.23 |
| 1F | 7.0 | 2.3 | " | " | 66.92 |

TABLE 6-continued

Samples for Thermal Stability Tests

| Sample | Solvent (%) | AI (%) | Surfactants (%) | Defoamer (%) | % Water |
|---|---|---|---|---|---|
| 1G | 7.5 | 1.7 | " | " | 67.04 |
| 1H | 7.5 | 2.0 | " | " | 66.73 |
| 1I | 7.5 | 2.3 | " | " | 66.42 |
| 1J | 8.0 | 1.7 | " | " | 66.54 |
| 1K | 8.0 | 2.0 | " | " | 66.23 |
| 1L | 8.0 | 2.3 | " | " | 65.92 |
| 1M | 8.0 | 2.0 | 21.00 | 0 | 69.00 |
| 1N | 8.0 | 2.0 | 18.08 | 0.40 | 71.47 |
| 1O | 5.75 | 2.0 | 18.08 | 0.40 | 73.72 |
| 1P | 8.0 | 2.0 | 15.16 | 0 | 74.84 |
| 2A | 6.0 | 1.7 | 23.37 | 0.40 | 68.54 |
| 2B | 6.0 | 2.0 | " | " | 68.23 |
| 2C | 6.0 | 2.3 | " | " | 67.92 |
| 2D | 7.0 | 1.7 | " | " | 67.54 |
| 2E | 7.0 | 2.0 | " | " | 67.23 |
| 2F | 7.0 | 2.3 | " | " | 66.92 |
| 2G | 7.5 | 1.7 | " | " | 67.04 |
| 2H | 7.5 | 2.0 | " | " | 66.73 |
| 2I | 7.5 | 2.3 | " | " | 66.42 |
| 2J | 8.0 | 1.7 | " | " | 66.54 |
| 2K | 8.0 | 2.0 | " | " | 66.23 |
| 2L | 8.0 | 2.3 | " | " | 65.92 |
| 2M | 8.0 | 2.0 | 21.00 | 0 | 69.00 |
| 2N | 8.0 | 2.0 | 18.08 | 0.40 | 71.48 |
| 2O | 5.75 | 2.0 | 18.08 | 0.40 | 73.72 |
| 2P | 8.0 | 2.0 | 15.16 | 0 | 74.84 |

Hot physical stability was evaluated by placing vials containing the samples in a heating block at 55° C. The samples were removed from the heating block and evaluated for their stability by visual examination of the sample after 1, 2, 3, and 4 weeks. After evaluation, the samples were returned to the heating block. The ME's were rated using the scale in Example 2 supra. Cold physical stability was evaluated by placing vials containing the samples in a freezer. The freezer was kept between 0° and 2° C. The samples were removed from the freezer and visually inspected after 1, 2, 3, and 4 weeks. After inspection, the samples were replaced in the freezer. The ME's were rated using the scale in Example 2 supra. An "X" indicates crystalization of the solid AI from solution. The results of both the hot and cold physical stability studies are reported in Table 7.

TABLE 7

Thermal Physical Stability Tests

| Sample # | Hot Physical Stability | | | | Cold Physical Stability | | | |
|---|---|---|---|---|---|---|---|---|
| | 1 wk | 2 wks | 3 wks | 4 wks | 1 wk | 2 wks | 3 wks | 4 wks |
| 1A | 0 | 0 | 0 | 0 | 0 | 0 | 0 | 0 |
| 1B | 0 | 0 | 0 | 0 | 0 | 0 | 0 | 0 |
| 1C | 0 | 0 | 0 | 0 | 0 | X | X | X |
| 1D | 0 | 0 | 0 | 0 | 0 | 0 | 0 | 0 |
| 1E | 0 | 0 | 0 | 0 | 0 | 0 | 0 | 0 |
| 1F | 0 | 0 | 0 | 0 | 0 | 0 | 0 | 0 |
| 1G | 0 | 0 | 0 | 0 | 0 | 0 | 0 | 0 |
| 1H | 0 | 0 | 0 | 0 | 0 | 0 | 0 | 0 |
| 1I | 0 | 0 | 1 | 0 | 0 | 0 | 0 | 0 |
| 1J | 0 | 0 | 0 | 0 | 0 | 0 | 0 | 0 |
| 1K | 0 | 0 | 0 | 0 | 0 | 0 | 0 | 0 |
| 1L | 0 | 0 | 0 | 0 | 0 | 0 | 0 | 0 |
| 1M | 0 | 0 | 1 | 1 | 0 | 0 | 0 | X |
| 1N | 0 | 5 | 5 | 5 | 0 | 0 | 0 | 0 |
| 1O | 0 | 5 | 5 | 5 | 5 | X | 5 | X |
| 1P | 5 | 5 | 5 | 5 | 0 | 0 | 0 | X |
| 2A | 0 | 0 | 0 | 0 | 5 | 5 | 0 | 0 |
| 2B | 0 | 0 | 0 | 0 | 5 | 5 | X | 0 |
| 2C | 0 | 0 | 0 | 0 | 5 | 5 | X | X |
| 2D | 0 | 0 | 0 | 0 | 5 | 5 | 0 | 0 |
| 2E | 0 | 0 | 0 | 0 | 5 | 5 | 0 | 0 |
| 2F | 0 | 0 | 0 | 0 | 5 | 5 | X | 0 |
| 2G | 0 | 0 | 0 | 0 | 0 | 0 | 0 | 0 |
| 2H | 0 | 0 | 0 | 0 | 0 | 0 | 0 | 0 |
| 2I | 0 | 0 | 0 | 0 | 0 | 0 | X | 0 |
| 2J | 0 | 0 | 0 | 0 | 0 | 0 | 0 | 0 |
| 2K | 0 | 0 | 0 | 0 | 0 | 0 | 0 | 0 |
| 2L | 0 | 0 | 0 | 0 | 0 | 0 | X | 0 |
| 2M | 0 | 0 | 0 | 0 | 0 | 0 | 0 | 0 |
| 2N | 0 | 0 | 0 | 0 | 5 | 5 | 0 | 5 |
| 2O | 0 | 0 | 0 | 0 | 0 | 0 | X | 0 |
| 2P | 0 | 0 | 1 | 5 | 1 | 5 | X | X |

The above data show many of the ME's of the invention have good hot and cold physical stability.

The ME's were also evaluated for their stability to freeze-thaw cycles. Samples of the above ME's were placed in a freezer which was kept at −10° C. After the samples had frozen, they were removed from the freezer and allowed to warm to room temperature. Once at room temperature, the samples were visually evaluated using the rating scale in Example 2. The samples were then returned to the freezer. The entire process was repeated two more times. The results of these freeze-thaw cycles, along with the initial appearance of the ME's, are reported in Table 8.

TABLE 8

| Sample # | Freeze-thaw Cycles | | | |
|---|---|---|---|---|
| | Initial | 1st Cycle | 2nd Cycle | 3rd Cycle |
| 1A | 0 | 0 | 0 | 0 |
| 1B | 0 | 0 | 0 | 0 |
| 1C | 0 | 0 | 0 | X |
| 1D | 0 | 0 | 0 | 0 |
| 1E | 0 | 0 | 0 | 0 |
| 1F | 0 | 0 | 0 | 0 |
| 1G | 0 | 0 | 0 | 0 |
| 1H | 0 | 0 | 0 | 0 |
| 1I | 0 | 0 | 0 | 0 |
| 1J | 0 | 0 | 0 | 0 |
| 1K | 0 | 0 | 0 | 0 |
| 1L | 0 | 0 | 0 | 0 |
| 1M | 0 | 0 | 0 | 0 |
| 1N | 0 | 0 | 0 | 0 |
| 1O | 0 | 0 | 5 | 5 |
| 1P | 0 | 5 | 5 | 0 |
| 2A | 0 | 0 | 0 | 0 |
| 2B | 0 | 5 | X | X |
| 2C | 0 | X | X | X |
| 2D | 0 | 0 | 0 | 0 |
| 2E | 0 | 0 | 0 | 0 |
| 2F | 0 | 0 | 0 | X |
| 2G | 0 | 0 | 0 | 0 |
| 2H | 0 | 0 | 0 | 0 |
| 2I | 0 | 0 | 0 | X |
| 2J | 0 | 0 | 0 | 0 |
| 2K | 0 | 0 | 0 | 0 |
| 2L | 0 | 0 | 0 | X |
| 2M | 0 | 0 | 0 | 0 |
| 2N | 0 | 0 | 0 | 0 |
| 2O | 0 | 0 | 0 | X |
| 2P | 0 | 0 | 0 | 0 |

The above data show many of the ME's of the invention have good freezethaw stability.

Example 6—Water Dilutability of AI's Useful in Agriculture

To demonstrate the applicability of the formulations of this invention to other AI's, the water dilutability of MC's containing the following water insoluble AI's at the following concentrations was determined.

AI3 = 2-chloro-1-(3-ethoxy-4-nitrophenoxy)-4-(trifluoromethyl)benzene
AI4 = 2,4-dinitro-6-octyl-phenyl crotonate
AI5 = α-butyl-α-(4-chlorophenyl)-1H-1,2,4-triazole-1-propanenitrile

| Component | Concentration % |
|---|---|
| AI3, 4, or 5 | 9.0 |
| Solvent 2 | 21.0 |
| Surfactant A | 49.0 |
| Surfactant E | 21.0 |

The MC's were prepared as described in Example 1. The water dilutability of these samples was determined as described in Example 2, using the same rating scale. The results are shown in Table 9. Sample 63 has the composition described above with AI 3, sample 64 has the composition described above with AI 4, and sample 65 has the 2O composition described above with AI 5.

TABLE 9

Water Dilutability of Other AI's

| % Water by Weight: | 0 | 10 | 20 | 30 | 40 | 50 | 60 | 70 | 80 | 90 | 98 |
|---|---|---|---|---|---|---|---|---|---|---|---|
| 63 | 0 | 0 | 0 | 1 | 2 | 3 | 1 | 0 | 0 | 0 | 0 |
| 64 | 0 | 0 | 0 | 0 | 3 | 3 | 1 | 0 | 0 | 0 | 0 |
| 65 | 0 | 0 | 0 | 0 | 2 | 3 | 2 | 0 | 0 | 0 | 0 |

These results in Table 9 indicate the microemulsions this invention are useful with a wide variety of low water soluble active ingredients.

While the invention has been described in sufficient detail for those skilled in the art to be able to make and use it, various alternatives, modifications, and improvements should become apparent from the foregoing disclosure without departing from the spirit and scope of the invention.

We claim:

1. Composition useful as a biocide consisting essentially of
    (A) one or more active ingredient compounds which are less than 1000 ppm soluble in water at room temperature and having a melting point of less than 100° C. selected from the group consisting of 4,5-dichloro-2-n-octyl-3-isothiazolone and 2-n-octyl-3-isothiazolone;
    (B) one or more non-polar, water immiscible solvent selected from the group consisting of benzyl alcohol, benzyl acetate, pine oil, phenethyl alcohol, xylene, phenoxyethanol, butyl phthalate, 2,2,4-trimethyl-1,3-pentanediol monoisobutyrate, and alkylbenzene, said solvent being capable of dissolving at least 5% by weight of (A) at room temperature;
    (C) a surfactant system consisting essentially of:
        (C1) one or more sulfated of sulfonated anionic surfactants having about 3-17% sulfation or sulfonation, selected from the group consisting of sulfated and/or sulfonated castor oil, sulfated and/or sulfonated ethoxylated alkylphenols, sulfated and/or sulfonated ethoxylated fatty alcohols, sulfated and/or sulfonated fatty acids, and sulfated alkanolamides; and
        (C2) one or more ethoxylated surfactant selected from the group consisting of ethoxylated ($C_{10}$–$C_{18}$)alkyl phosphate monoesters and/or diesters and/or triesters, ethoxylated ($C_{10}$–$C_{18}$)alkaryl phosphated monoesters and/or diesters, ethoxylated ($C_8$–$C_{20}$)monoalkyl- or dialkylphenols, ethoxylated alkylamides, ethoxylated alkanols, and ethoxylated cator oil;
    (D) 0 to 99.9% by weight water; and optionally,
    (E) one or more adjuvants selected from the group consisting of antifreeze agents, water soluble inorganic salts, thickeners, and defoamers;
    wherein
        the weight ratio of (C1) to (C2) being about 10/90 to 90/10;
        the weight ratio of said (A) to (B) being about 95/5 to about 1/99, and
        the weight ratio of said (A) to (C) being about 1/99 to about 86/14;
        said composition being thermodynamically stable and clear, opalescent, or only slightly cloudy at all levels of water dilution up to 99.9%.

2. A composition according to claim 1 wherein the weight ratio of (A) to (C) is about 1/99 to 30/70.

3. A composition according to claim 1 wherein (B) is a mixture of benzyl alcohol and pine oil.

4. A composition according to claim 1 wherein (C1) is an anionic, sulfated and/or sulfonated castor oil.

5. A composition according to claim 1 wherein (C2) is selected from the group consisting of an anionic, ethoxylated ($C_{10-18}$)alkyl phosphate and a nonionic, ethoxylated ($C_8$–$C_{20}$)mono- and/or dialkyl phenol.

6. A composition according to claim 1 wherein the weight ratio of (C1) to (C2) is about 30/70 to 70/30.

7. A composition according to claim 1 wherein the weight ratio of (C1) to (C2) is about 50/50 to 70/30.

8. A composition according to claim 1 wherein the weight ratio of (A) to (B) is about 50/50 to about 10/90.

9. A composition according to claim 1 wherein (A) is 4,5-dichloro-2-n-octyl-3-isothiazolone, (B) is benzyl alcohol, (C1) is an anionic, sulfated and/or sulfonated castor oil, fatty acid, or fatty ester, (C2) is selected from the group consisting of an anionic, ethoxylated ($C_{10-18}$)alkyl phosphate and a nonionic, ethoxylated ($C_8$–$C_{20}$)mono- and/or dialkyl phenol, the weight ratio of (C1) to (C2) being about 30/70 to 70/30, the weight ratio of (A) to said (B) being about 50/50 to about 10/90, and the weight ratio of (A) to the (C) being about 1/99 to 30/70.

10. Composition according to claim 1 in the form of a microemulsion concentrate having 0% water.

11. Composition according to claim 1 in the form of a microemulsion having about 1 to 99.9% by weight water.

12. Process of controlling undesirable bacteria and fungal growth in a pulp or paper making process comprising introducing a composition according to claim I in said pulp or paper making process in amounts sufficient to control said growth.

* * * * *